US00PP28738P2

(12) United States Plant Patent
Ault

(10) Patent No.: US PP28,738 P2
(45) Date of Patent: Dec. 5, 2017

(54) ***PHLOX* PLANT NAMED 'RUNNING WITH SCISSORS'**

(50) Latin Name: ***Phlox subulata*×*Phlox bifida***
Varietal Denomination: Running With Scissors

(71) Applicant: James Robert Ault, Libertyville, IL (US)

(72) Inventor: James Robert Ault, Libertyville, IL (US)

(73) Assignee: CHICAGOLAND GROWS, INC., Glencoe, IL (US)

( * ) Notice: Subject to any disclaimer, the term of this patent is extended or adjusted under 35 U.S.C. 154(b) by 102 days.

(21) Appl. No.: 14/998,606

(22) Filed: Jan. 26, 2016

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Anne Grunberg
(74) *Attorney, Agent, or Firm* — Penny J. Aguirre

(57) ABSTRACT

A new cultivar of *Phlox* plant named, 'Running With Scissors', that is characterized by its a very vigorous, broad spreading plant habit that readily layers into a groundcover, its very large flowers 2.5 cm in diameter and medium violet pink in color and aging to light violet pink with irregular pigments, its flowers that produce a faint, sweet hay fragrance, its light, repeat bloom in autumn in some years, its flowers that cover 90% to 100% of the plant at peak bloom, and its distinctly bifid leaves with a deep cleft 6 mm in depth and width.

2 Drawing Sheets

Botanical classification: *Phlox subulata*×*Phlox bifida*.
Cultivar designation: 'Running With Scissors'.

BACKGROUND OF THE INVENTION

The present invention relates to a new and distinct cultivar of *Phlox* plant, botanically known as *Phlox* 'Running With Scissors' and will be referred to hereafter by its cultivar name, 'Running With Scissors'. The new cultivar represents a new herbaceous perennial grown for landscape use.

The new invention arose from an ongoing controlled breeding program by the Inventor in Glencoe, Ill. The objectives of the breeding program are to develop improved cultivars of interspecific hybrids of *Phlox* with novel ornamental traits such as unique flower colors, plant habits, flower fragrance and adaptability to garden conditions in the upper Midwest (U.S.D.A. Zone 5) and similar climates.

'Running With Scissors' was derived from a cross made in May of 2008 under controlled conditions (that excluded natural pollinators) between *Phlox subulata* 'McDaniel's Cushion' (not patented) as the female parent and an unnamed and unpatented plant of *Phlox bifida* as the male parent. 'Running With Scissors' was selected in May of 2010 as a single unique plant amongst the resulting seedlings.

Asexual propagation of the new cultivar was first accomplished by shoot tip cuttings by the Inventor in June of 2010 in Glencoe, Ill. Asexual propagation by shoot tip cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Running With Scissors' as a unique cultivar of *Phlox*.

1. 'Running With Scissors' exhibits a very vigorous, broad spreading plant habit that readily layers into a groundcover.
2. 'Running With Scissors' exhibits very large flowers 2.5 cm in diameter (considered large for a moss *phlox*) that are medium violet pink in color and aging to light violet pink with irregular pigments.
3. 'Running With Scissors' exhibits flowers that produce a faint, sweet hay fragrance, unique for a moss *phlox*.
4. 'Running With Scissors' exhibits a light, repeat bloom in autumn in some years; a unique trait for a moss *phlox*.
5. 'Running With Scissors' exhibits flowers that cover 90% to 100% of the plant at peak bloom.
6. 'Running With Scissors' exhibits distinctly bifid leaves with a cleft 6 mm in depth and width; the deepest cleft the Inventor has observed on a hybrid moss *phlox* that he has tested.

The female parent of 'Running With Scissors', 'McDaniel's Cushion', differs from 'Running With Scissors' in having flowers that are medium dark, magenta pink in color, in having floral pigments uniform across the upper petal surfaces, in having a striae that is laterally diffused and almost forming a ring that is deep magenta raspberry in color, in having petal lobes that have broad rounded tips with small clefts that are 2 mm in depth and 2 mm in width and in having flowers that are not fragrant. The male parent of 'Running With Scissors', an unnamed plant of *Phlox bifida*, differs from 'Running With Scissors' in having flowers that are white in color and non-fragrant, in having leaves that are longer and pubescent, and in lacking repeat bloom in the fall. 'Running With Scissors' can also be compared to the *Phlox* cultivars 'Fort Hill' (not patented) and 'Blue Hills' (not patented). 'Fort Hill' is similar to 'Running With Scissors' in having flowers that produce bifid petal lobes with a distinct cleft and in having a repeat blooming habit in the fall. 'Fort Hill' differs from 'Running With Scissors' in having striae that are deep red-purple in color, in having flowers that are non-fragrant, in having flowers that are smaller in diameter with smaller cleft size (3 mm in depth and width) on the petal lobes. 'Blue Hills' is similar to 'Running With Scissors' in having flowers that produce bifid petal lobes with a distinct cleft and in having large sized flowers. 'Blue Hills' differs from 'Running With Scissors' in having flowers that are reddish violet in color and aging to a distinctly lighter bluish violet color with no red tones, in having flowers that are non-fragrant, in having foliage margins that are not ciliate and in having a smaller cleft size (3 mm in depth and width) on the petal lobes.

BRIEF DESCRIPTION OF THE DRAWINGS

The accompanying colored photographs illustrate the overall appearance and distinct characteristics of the new *Phlox*. The photographs were taken of 'Running With Scissors' as grown in a trial garden in Glencoe, Ill.

The photograph in FIG. 1 provides a view of the plant habit of a block of fifteen 4 year-old plants of 'Running With Scissors'.

Figure 1:
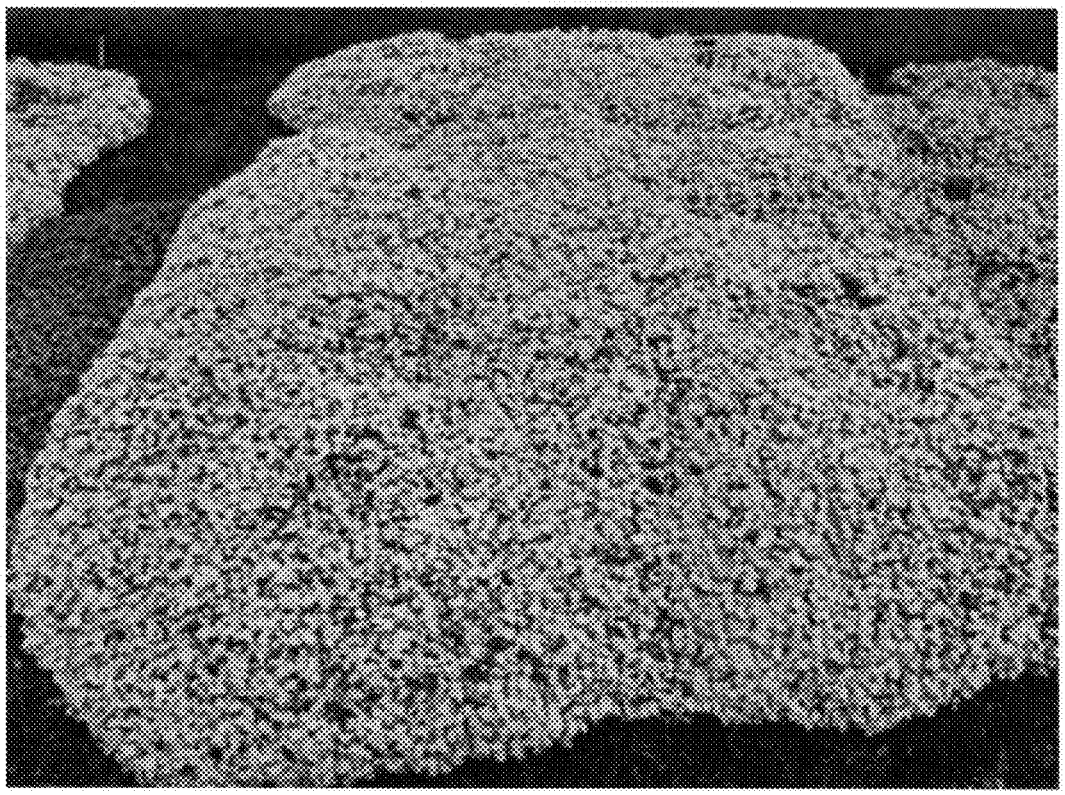
Figure 2:
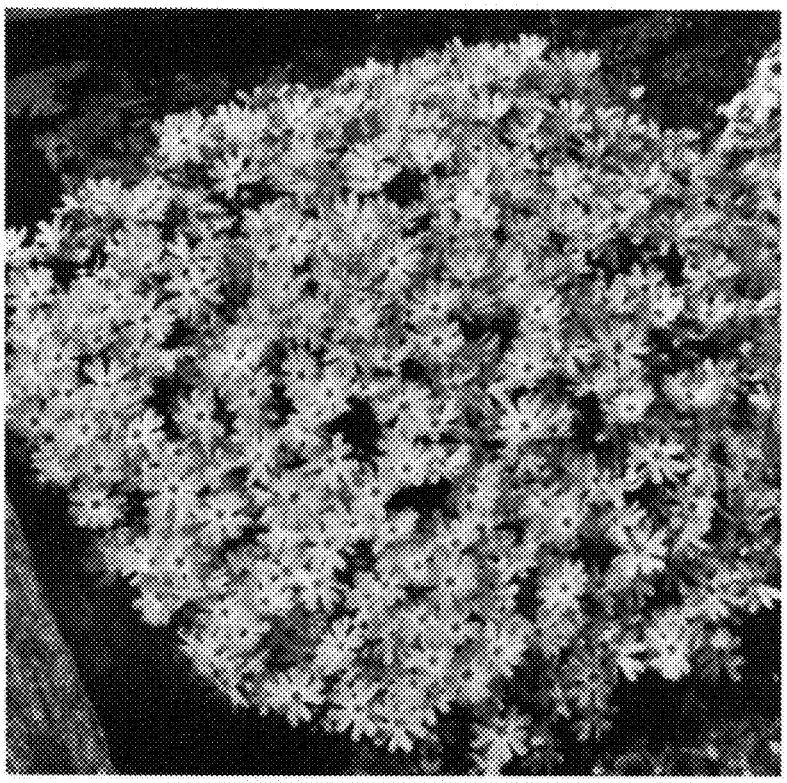

The photograph in FIG. 2 provides a view of the original plant of 'Running With Scissors' 2 years in age.

Figure 3:
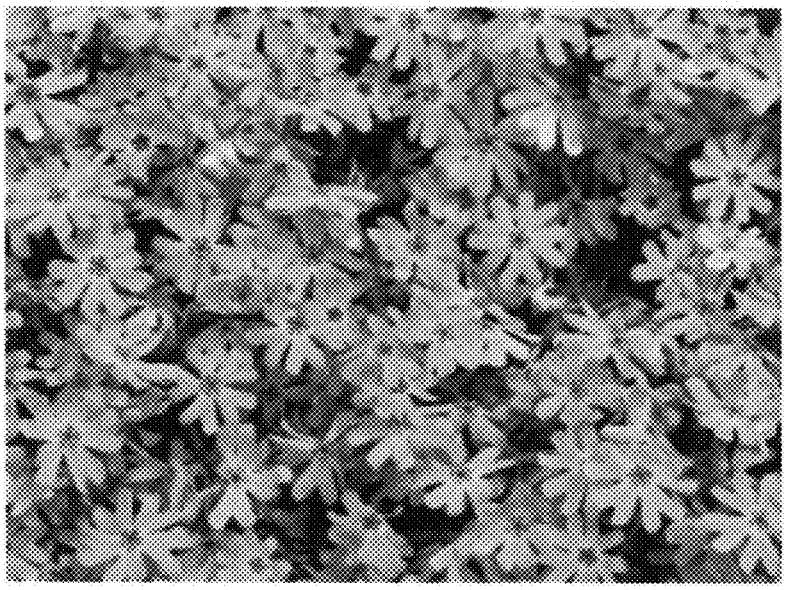

The photograph in FIG. 3 provides a close-up view of the inflorescences of a 4 year-old plant of 'Running With Scissors'.

The colors in the photographs are as close as possible with the photographic and printing technology utilized and the color values cited in the Detailed Botanical Description accurately describe the colors of the new *Phlox*.

DETAILED BOTANICAL DESCRIPTION OF THE PLANT

The following is a detailed description of nine month-old plants of the new cultivar as grown in 4-inch containers in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Four to six weeks beginning in mid to late April in northern Illinois, light re-bloom has been observed in some years in autumn in northern Illinois.

*Plant habit*.—Very vigorous, broad spreading plant habit that readily layers into a groundcover.

*Height and spread*.—In-ground trial plants 2 years in age; 51 cm in width and 18 cm in height at peak bloom, in-ground trial plants 4 years in age; 97 cm in width and 18 cm in height at peak bloom.

*Hardiness*.—At least hardy in U.S.D.A. Zones 4 to 8.

*Diseases and pests*.—Very good resistance to powdery mildew (caused by *Erysiphe cichoracearum*) has been observed.

*Root description*.—Fibrous.

*Growth rate*.—Very vigorous.

*Propagation*.—Shoot tip cuttings.

*Root development*.—Shoot tip cuttings will root under mist in 4 to 5 weeks in late spring to early summer, rooted cutting will fully root in a 2.5 inch pot in about 3 months and when tranplanted in fall and overwintered in a 4-inch pot, they will bloom the following spring.

Stem description:

*Stem size*.—An average of 10 cm in length and 1.5 mm in width.

*Stem shape*.—Rounded.

*Stem strength*.—Strong.

*Stem color*.—143C, heavily suffused with 183C at the base.

*Stem surface*.—Smooth, slightly glossy, and densely covered with wooly hairs about 1 mm in length.

*Stem aspect*.—Held upright to trailing.

*Internode length*.—An average of 1 cm.

*Branching habit*.—Well branched an average of 10 lateral stems per main stem.

Foliage description:

*Leaf shape*.—Narrowly elliptic to linear.

*Leaf division*.—Simple.

*Leaf base*.—Truncate to clasping.

*Leaf apex*.—Subacute.

*Leaf venation*.—Pinnate, inconspicuous, matches leaf color on upper and lower surfaces.

*Leaf margins*.—Entire and sparsely covered in fine hairs about 1 mm in length.

*Leaf attachment*.—Sessile.

*Leaf arrangement*.—Opposite.

*Leaf surface texture*.—Smooth and shiny on upper and lower surfaces.

*Leaf color*.—Upper surface; 138A, lower surface; 138B.

*Leaf size*.—An average of 1.5 cm in length and 3 mm in width.

*Leaf quantity*.—An average of 16 leaves (8 pairs) on a stem.

*Leaf fragrance*.—None.

Flower description:

*Inflorescence type*.—Panicle on terminus of main stems and lateral branches.

*Lastingness of inflorescence*.—About 3 to 4 weeks from the opening of the first flower to senescence of last flower, individual flower lasts about 5 days.

*Inflorescence size*.—An average of 4.5 cm in height and 6 cm in diameter.

*Flower fragrance*.—Faint, sweet hay fragrance.

*Flower number*.—An average of 4 per inflorescence.

*Flower aspect*.—Upright to outward.

*Flower bud*.—Spatulate in shape, acute apex, an average of 1.8 cm in length and up to 3 mm in width, color; petal portion 92A to 92D near base and calyx portion a blend of 85B to 85C, 144D near the base.

*Flower form*.—Salverform.

*Flower size*.—An average of 1.5 cm in height and 2.5 cm in diameter.

*Corolla tube*.—An average of 1.4 cm in length and 2 mm in width, color; 85A to 85D with 144D near base, glabrous and satiny surface texture.

*Corolla lobes*.—5, obcordate in shape, held nearly horizontally when fully open, slightly overlapping near base, an average of 12 mm in length and 9 mm in width, bifid with a deep cleft 6 mm in depth and width, apex of lobes rounded, base broadly cuneate and fused to tube, entire margins, color: upper surface when opening; a blend of 76A and 85A and N155A (irregularly dispersed) and a distinct pair of striae 83A to 83B near base, lower surface when opening; 85A to 85D, upper surface when fully open; 85A to 85D with N155A (irregular dispersed) and a distinct pair of striae 83A to 83B near base, lower surface when fully open; 92B to 92D, glabrous and satiny surface texture on upper and lower surfaces.

*Calyx*.—Campanulate in form, comprised of fused sepals with linear shaped sepal tips free, an average of 7 cm in length and 2.5 mm in width.

*Sepals*.—5, primarily fused with free tips, linear in shape, entire margins, fused base (about 80%), aristulate apex, an average of 7 mm in length and 1 mm in width, inner surface texture; glabrous and shiny, outer surface texture; densely covered with wooly hairs about 1 mm in length, color on inner and outer surface; 137A to 137D, getting lighter in color near the base.

*Peduncles*.—Rounded in shape, an average of 2.5 cm in length and 1.5 mm in width, held upright to outward, surface; color; 143A to 143C, smooth, slightly glossy, and densely covered with wooly hairs about 1 mm in length.

*Pedicels*.—Rounded to oval in shape, an average of 2.3 cm in length and 1 mm in width, held at an average angle of 15° to peduncle, color; 143A to 143C and heavily suffused with 183A, surface is smooth, slightly glossy, and densely covered with wooly hairs about 1 mm in length.

Reproductive organs:

*Gynoecium*.—1 pistil, stigma; tri-lobed, each lobe is about 1.5 mm in length and 12D in color, style is about 1 cm in length and 0.3 mm in width, 149D in color, ovary; superior, rotund to oval in shape, about 1 mm in length and 0.7 mm in width, and 143C in color.

*Androcoecium*.—5 stamens, anthers; dorsifixed, oblong in shape, an average of 1 mm in length, and 17A in color, filaments; adnate to petals, an average of 6 mm in length and 155C in color, pollen is abundant in quantity and 17A in color.

*Seeds*.—None observed.

It is claimed:

1. A new and distinct cultivar of *Phlox* plant named 'Running With Scissors' as herein illustrated and described.

* * * * *